United States Patent [19]

Hillshafer

[11] Patent Number: 4,478,941

[45] Date of Patent: Oct. 23, 1984

[54] METHOD FOR DETERMINING COMPONENT RATIOS EMPLOYED TO PREPARE POLYMERS

[75] Inventor: Douglas K. Hillshafer, Lake Jackson, Tex.

[73] Assignee: The Dow Chemical Company, Midland, Mich.

[21] Appl. No.: 444,632

[22] Filed: Nov. 26, 1982

[51] Int. Cl.³ .................. C09K 3/00; G01N 31/22; G01N 33/44
[52] U.S. Cl. ........................... 436/56; 436/85; 436/178; 436/161; 525/51
[58] Field of Search .............. 436/56, 85, 161, 174, 436/178, 57–59; 525/51

[56] References Cited

U.S. PATENT DOCUMENTS 3,600,133 8/1971 Price et al. ..................... 436/56

OTHER PUBLICATIONS

Detection of Some Antioxidants in Vulcanized Rubber Stocks, Hively et al., Analytical Chemistry, vol. 27, No. 1, Jan. 55, pp. 100–103.

*Primary Examiner*—Michael S. Marcus
*Assistant Examiner*—Joseph P. Carrier

[57] ABSTRACT

The ratio of two or more components employed to produce a thermoset or thermoplastic polymer are determined by analyzing the resultant polymer to determine ratio of tracer elements therein which were incorporated separately into each of the components employed to produce the polymer.

6 Claims, No Drawings

METHOD FOR DETERMINING COMPONENT RATIOS EMPLOYED TO PREPARE POLYMERS

BACKGROUND OF THE INVENTION

The present invention concerns a method for determining the ratio of components employed to prepare polymers which are prepared by blending at least two components.

In the preparation of polyurethane thermoset or thermoplastic polymers, cured epoxy resins, and polyester resins, cured vinyl ester resins and the like, two or more components each containing one or more different components are blended together and subsequently cured either as coatings, castings or the like. The resultant properties are dependent upon predetermined component ratios. The actual production of such polymers employ metering and mixing equipment whose settings can become out of balance with that which is desired thereby resulting in misproportioning of the components which in turn results in alternation of the properties of the cured polymer composition.

The present invention provides a method for analyzing the resultant polymer to determine the ratio at which the components were blended to produce such polymer.

SUMMARY OF THE INVENTION

The present invention pertains to a method for determining the ratio at which the components of a polymer prepared by blending and subsequently curing two or more compositions which compositions contain one or more components are mixed; which method comprises:

(A) employing a separate tracer compound in a known quantity in each of said compositions;

(B) conducting the usual mixing and curing procedures normally employed to prepare the polymer from mixing of each of said compositions;

(C) subjecting a representative sample of the cured polymer to a condition for preparing small particles thereof;

(D) subjecting said small particles to solvent extraction with a solvent system for a time sufficient to extract analyzable quantities of said tracer compounds;

(E) separating said solvent from the polymer particles;

(F) analyzing said separated solvent so to determine the ratio of each of said tracer compounds; and (G) calculating the ratio of said compositions employed in the preparation of said polymer from the analysis of the tracer compounds determined in step (F); and wherein (1) said solvent system is one in which each of the tracer compounds is soluble and which does not react with any of the tracer compounds or the polymer; and (2) said tracer compounds are non-reactive with any of the components which are blended together to prepare the polymer; and have a boiling point above the temperature at which the polymer is prepared or post cured, whichever is higher.

DESCRIPTION OF THE PREFERRED EMBODIMENTS

Suitable polymers in which the present method can be utilized are polyurethanes, polyesters, vinyl esters, epoxy resins, polyamides, and the like.

The method of the present invention is particularly suitable for use in determining the ratio of compositions employed in preparing polyurethanes.

In the preparation of polyurethanes, either foamed or unfoamed, at least two compositions are blended together to form the polymer. One such composition is commonly referred to as the (B) side which usually contains one or more reactive polyols, catalysts, and optionally, cell control agents, blowing or foaming agents, modifiers, fillers, fire retardant agents and the like. The other composition, commonly referred to as the (A) side usually contains the polyisocyanate, but may contain other components if desired.

The particular tracer compounds to be employed in the present invention of course depends upon the particular components employed to prepare the polymer and the conditions at which the components are subjected either during preparation or any post curing and also including any exotherm. It is necessary that none of the tracer compounds be lost through volatilization, reaction or the like.

For polyurethanes, particularly suitable tracer compounds are the aromatic dicarboxylic acid esters such as, for example, dimethyl phthalate, dimethyl terephthalate, diethyl phthalate, diethyl terephthalate, dipropyl phthalate, dipropyl terephthalate, dibutyl phthalate, dibutyl terephthalate, dipentyl phthalate, dipentyl terephthalate, dihexyl phthalate, dihexyl terephthalate, diheptyl phthalate, diheptyl terephthalate, dioctyl phthalate, dioctyl terephthalate, and the like.

For any polymer system, a suitable tracer can be routinely determined by checking its solubility in the composition in which it is to be employed and at the levels at which it is to be employed making sure that it does not contain groups which are reactive with any of the components employed to prepare the polymer.

Likewise, suitable solvents can be determined by mixing the tracer compounds therewith and checking for suitable solubility.

Particularly suitable solvents would include, dimethyl formamide, dimethylsulfoxide, tetrahydrofuran, iso-octane, methylene chloride, acetone, mixtures thereof and the like.

The only other criteria for the solvent other than solubility of the tracer compounds therein is that the solvent not react with the tracer compounds or the polymer during the time in which they are in contact with each other.

The polymer to be tested by the method of the present invention can be sawed, chipped, cracked, pulverized or any method which will produce a particle size sufficient to provide sufficient surface area for extraction of the tracer compounds with the solvent.

When the particular solvent and tracer compounds have been determined, then the necessary experiments can be run to determine any constants for making the calculations or calibrating any instruments.

Suitable means for determining the ratio of the concentration of the tracer elements in the solvent which corresponds to the ratio of concentration of the tracer compounds in the polymer include, for example, infrared, liquid phase chromatograph, gel permeation chromatography and the like. Particularly suitable is liquid phase chromatography utilizing an ultraviolet detector such as a Hewlett Packard 1081-B Liquid Chromatograph with a Waters Model 440 U.V. detector at 254 nm interfaced with Hewlett Packard 3388-A integrator/terminal arrangement.

The following example is illustrative of the invention but is not to be construed as to limiting the scope thereof in any manner.

EXAMPLE 1

To the resin kettle (or B side) of an Admiral 400 2 HP RIM machine, about 127 lbs. (57,658 grams) of a polyol elastomeric formulation was charged. Next, 0.43 lbs. (196.61 grams) of dibutylphthalate (DBP) was also added to the contents of this resin kettle. About 60 lbs. (27,240 grams) of a liquid isocyanate was charged into the isocyanate kettle (or A side) along with 0.031 lbs. (13.62 grams) of dioctylteraphthalate (DOTP). The contents of both kettles were separately well mixed via kettle agitators and pump recirculation for at least 30 minutes (1800 s).

Sample plaques for evaluation were produced by first setting the A and B side pumps to some desired level, shooting a calibration shot to determine the actual A/B weight ratio of a part produced when those pump settings are used, and then shooting a ⅛" thick test plaque at that A/B weight ratio. The entire process was then repeated several more times, each time varying the A and B pump settings and establishing the respective A/B weight ratios for the ensuing samples.

Several plaques were obtained over a wide range of polyol to isocyanate weight ratios, and small sections were cut from each plaque. Each section from each sample was then sliced into about 10-15 grams of ~⅛" cubes. The cubes were then placed in separate glass jars, along with 38 grams of a solvent (33 pbw tetrahydrofuran+66 pbw iso-octane+1 gram n-butylamine). Each jar was sealed with a cap and mechanically shaken for approximately 30 minutes (1800 s). The solvent of each jar was then poured into separate vials; approximately 1 gram of anhydrous sodium sulfate was also added to each vial to remove water. Each vial was capped, shaken, and after a few seconds (when the $Na_2SO_4$ had mostly settled out of solution) the remaining solvent was passed through a GELMAN ACRODISK® CR 0.45 μm filter via a syringe and into a small sampling vial. Each vial was finally capped with a rubber septum and the vial contents were analyzed via a Hewlett Packard 1081-B Liquid Chromatograph.

The Liquid Chromatograph (L.C.) solvent used here was the same as was employed for the extraction. The L.C. column was a Waters 8 cm, 5μ silica gel L.C. column. Interfaced with the L.C. was a Hewlett Packard 3388-A integrator for analyzing peak retention times and heights. A Waters Model 440 U.V. apparatus at 254 nm was used as the detector. Each vial for the L.C. was analyzed five times to determine the accuracy of this technique.

The L.C. separates the tracers (DBP, DOTP) via the L.C. column, while the Waters U.V. detector monitors the exiting fluids from the column to determine the quantitative presence of the tracers. The integrator quantitatively displays the peaks with heights proportioned to the tracer concentration.

EXPERIMENTAL RESULTS

Ratios of the peak heights, $r_h$, were calculated as below:

$$r_h = \frac{DOTP \text{ Peak Height}}{DBP \text{ Peak Height}} \quad (1)$$

Since each extraction sample was analyzed five times, the $r_h$ values were averaged to obtain $\bar{r}_h$ for each sample.

For one sample, #5, the actual A/B weight ratio (by calibration) was 0.74. For this same sample, though, $\bar{r}_h = 0.40$. Therefore, if $\bar{r}_h$ was always proportional to the weight ratio, A/B, then:

$$\bar{r}_h k = \frac{A}{B}.$$

In this case 0.40 k=0.74 or k=1.86. Therefore, 1.86 $\bar{r}_h$=A/B, and the relationship between $\bar{r}_h$ and A/B was found experimentally.

Table I below gives the plaque sample number, the A/B ratio determined by calibration, $\bar{r}_h$, the calculated A/B ratio (=1.86 $\bar{r}_h$) and the error (=A/B actual − A/B calculated).

TABLE I

| Sample | A/B Actual | $\bar{r}_h$ | A/B Calculated | Error |
|---|---|---|---|---|
| 1 | 0.67 | 0.36 | 0.67 | 0.00 |
| 3 | 0.69 | 0.36 | 0.67 | 0.02 |
| 5 | 0.74 | 0.40 | 0.74 | 0.00 |
| 7 | 0.56 | 0.31 | 0.58 | −0.02 |
| 9 | 0.55 | 0.29 | 0.54 | 0.01 |

Above, it was shown that the L.C. method for determining A/B ratios were within 0.02 units over a wide A/B range.

I claim:

1. A method for determining the mixing ratio of two or more compositions containing at least one component in each of such compositions which compositions are mixed together and subsequently cured to form a polymer; which method comprises:
   (A) adding a separate tracer compound in a known quantity to each of said compositions each of said separate tracers having different compositions;
   (B) mixing and curing each of said compositions and respective tracers to form a cured polymer;
   (C) subjecting a representative sample of the cured polymer to a condition for preparing small particles thereof;
   (D) subjecting said small particles to solvent extraction with a solvent system for a time sufficient to extract analyzable quantities of said different tracer compounds;
   (E) separating said solvent from the polymer particles;
   (F) analyzing said separated solvent so as to determine the ratio of each of said different tracer compounds; and
   (G) calculating the ratio of said composition employed in the preparation of said polymer from the analysis of the tracer compounds determined in step (F); and wherein
   (1) said solvent system is one
      (a) in which each of the different tracer compounds is soluble and (b) which does not react with any of the different tracer compounds or the polymer; and (2) each of said different tracer compounds (a) is not reactive with any of the components which are blended together to prepare the polymer;

(b) is not reactive with any other tracer compound employed; and (c) has a boiling point above the temperature at which the polymer is prepared or post cured, whichever is higher.

2. A method of claim 1 wherein step (F) is conducted with a liquid phase chromatograph with an ultraviolet detector.

3. A method of claim 1 wherein said polymer is a polyurethane or a cured epoxy resin.

4. A method of claim 3 wherein (a) said polymer is a polyurethane, prepared by mixing (A) a polyol-containing composition and (B) a polyisocyanate-containing composition; (b) one tracer compound is diotcyl terephthalate and the other is dibutyl phthalate; and (c) said solvent system is a mixture containing 33% tetrahydrofuran, 66% iso-octane, 1% n-butylamine, the percentages being by weight.

5. A method of claim 3 wherein step (F) is conducted with a liquid phase chromatograph with an ultraviolet detector.

6. A method of claim 4 wherein step (F) is conducted with a liquid phase chromatograph with an ultraviolet detector.

* * * * *